United States Patent [19]

Barnish et al.

[11] 3,971,783

[45] July 27, 1976

[54] 4-AMINOQUINAZOLINE DERIVATIVES AS CARDIAC STIMULANTS

[75] Inventors: Ian Thompson Barnish, Ramsgate; David Alexander Cox, Canterbury; Anthony Garth Evans, Sandwich, all of England

[73] Assignee: Pfizer Inc., New York, N.Y.

[22] Filed: Apr. 26, 1974

[21] Appl. No.: 464,673

Related U.S. Application Data

[63] Continuation-in-part of Ser. No. 444,656, Feb. 21, 1974, abandoned.

[30] Foreign Application Priority Data

Mar. 7, 1973 United Kingdom............. 11018/73

[52] U.S. Cl.................. 260/256.4 Q; 260/256.5 R; 424/251
[51] Int. Cl.²............... C07D 401/12; C07D 417/12
[58] Field of Search............. 260/256.4 Q, 256.5 R, 260/250 A

[56] References Cited

UNITED STATES PATENTS

| | | | |
|---|---|---|---|
| 3,346,452 | 10/1967 | Carney | 260/256.4 Q |
| 3,637,699 | 1/1972 | Gabel | 260/256.4 Q |
| 3,900,476 | 8/1975 | Renis et al. | 260/256.4 Q |

OTHER PUBLICATIONS

Morrison et al., "Organic Chemistry," pp. 473–476, (1966).

*Primary Examiner*—Alton D. Rollins
*Assistant Examiner*—David E. Wheeler
*Attorney, Agent, or Firm*—Connolly and Hutz

[57] ABSTRACT

Certain novel 7-alkoxy-4-(N-[ω-(heteroaryl)alkyl-]amino)quinazoline compounds, optionally bearing an alkyl or substituted alkyl group at the 2-position, an alkyl, benzyl, phenyl or alkoxyphenyl group on the 4-amino nitrogen atom, an alkyl or alkoxy group at the 5-position, and an alkyl alkoxy, hydroxy or amino group at the 6-position; and the acid-addition salts thereof. Compounds are cardiac stimulants.

9 Claims, No Drawings

4-AMINOQUINAZOLINE DERIVATIVES AS CARDIAC STIMULANTS

CROSS-REFERENCE TO RELATED APPLICATIONS

This application is a continuation-in-part of our co-pending application, Ser. No. 444,656, filed Feb. 21, 1974, now abandoned.

BACKGRUND OF THE INVENTION

1. Field of the Invention

This invention relates to certain novel organic chemical compounds, which are valuable in the art as cardiac stimulants. These chemical compounds are identified as quinazoline derivatives, and more specifically, they are 7-alkoxy-4-(N-[ω-(heteroaryl)alkyl]amino)-quinazoline derivatives, optionally bearing further substituents at the 2-, 5- and 6-positions, and on the 4-amino nitrogen atom. The compounds are useful in the curative or prophylactic treatment of cardiac conditions such as congestive heart failure, angina pectoris, cardiac arrhythmias and acute heart failure.

2. Description of the Prior Art

Quinazoline compounds are a well-known class of organic compounds, some of which are reported to have useful therapeutic properties. U.S. Pat. No. 3,517,005 discloses 4-aminoquinazoline derivatives with hypotensive and bronchodilatory activity, and U.S. Pat. No. 3,511,836 reports hypotensive 2,4-diaminoquinazolines. Scarborough et al., in the Journal of Organic Chemistry, 27, 957 (1961), reported the preparation of several 4-(1-substituted 3-pyrrolidinylmethylamino)quinazolines.

SUMMARY OF THE INVENTION

It is an object of the instant invention to provide novel quinazoline compounds of formula:

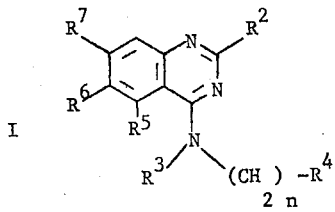

I and the acid-addition salts thereof;
wherein
$R^2$ is selected from the group consisting of hydrogen, alkyl having from one to six carbon atoms, hydroxyalkyl having from one to six carbon atoms and alkoxyalkyl having from two to six carbon atoms;
$R^3$ is selected from the group consisting of hydrogen, benzyl, alkyl having from one to six carbon atoms, phenyl and alkoxyphenyl having from one to six carbon atoms in said alkoxy group;
$R^4$ is selected from the group consisting of pyridyl, quinolyl, thiazolyl, imidazolyl, pyrazinyl, indolyl, hydroxypyridyl, alkylpyridyl having from one to six carbon atoms in said alkyl and alkylthiazolyl having from one to six carbon atoms in said alkyl group;
$R^5$ is selected from the group consisting of hydrogen, alkyl having from one to six carbon atoms and alkoxy having from one to six carbon atoms;
$R^6$ is selected from the group consisting of hydrogen, alkyl having from one to six carbon atoms, alkoxy having from one to six carbon atoms, hydroxy and amino;
$R^7$ is alkoxy having from one to six carbon atoms; and
$n$ is 1, 2, 3 or 4;
provided that $R^4$ is linked to $(CH_2)_n$ through a ring-carbon atom;
said quinazolines being of value as cardiac stimulants and being useful for the curative or prophylactic treatment of cardiac conditions such as congestive heart failure, angina pectoris, cardiac arrhythmias and acute heart failure.

A preferred group of quinazolines of this invention is the group of compounds of formula I, wherein $R^4$ is pyridyl, particularly 2-pyridyl; and especially valuable members of this series are those compounds of formula I, wherein $R^4$ is pyridyl, $R^2$ and $R^3$ are each hydrogen or methyl, $R^5$ is hydrogen, and $R^6$ and $R^7$ are each alkoxy having from one to six carbon atoms. The preferred configuration for $(CH_2)_n$ is an ethylene group.

By virtue of its outstanding therapeutic properties, a particularly desirable compound of this invention is 6,7-dimethoxy-4-(N-methyl-2[2-pyridyl]ethylamino)-quinazoline.

DETAILED DESCRIPTION OF THE INVENTION

As indicated hereinbefore, the object of the instant invention is to provide novel quinazolines of formula I. Several general methods are useful for the preparation of the said quinazolines, and six general methods are not to be discussed and described in detail. For the sake of convenience, they will be designated as Methods A, B, C, D, E and F.

Method A is useful for the preparation of the compounds of formula I, wherein $R^2$ selected from the group consisting of hydrogen, alkyl and alkoxyalkyl, $R^6$ is selected from the group consisting of hydrogen, alkyl and alkoxy and $R^3$, $R^4$, $R^5$, $R^7$ and n are as defined previously. Method A comprises the reaction of a compound of formula II with a amine of formula $R^3$—NH—$(CH_2)_n$—$R^4$, wherein X is selected from the group

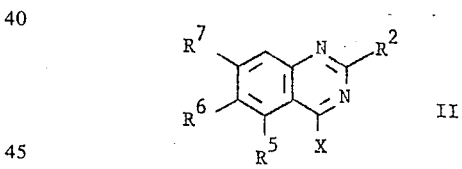

II consisting of chloro, bromo, alkoxy having from one to six carbon atoms and alkylthio having from one to six carbon atoms. The preferred configuration of X is chloro. The reaction is normally carried out by contacting the reactants in an appropriate solvent system, at a temperature in the range from about 50°C to about 170°C, and preferably from about 75°C to about 150°C. Appropriate solvents are those which will serve to dissolve at least one of the reactants, and will not adversely interact with either the starting reagents or the product. Examples of such solvents are aromatic hydrocarbons, such as benzene, toluene and xylene; ethers such as diethyl ether, tetrahydrofuran, dioxane and dialkyl ethers of ethylene glycol, propylene glycol and diethylene glycol; lower alkanols, such as methanol, ethanol and isopropanol; ethylene glycol; halogenated hydrocarbons, such as chloroform, methylene chloride and 1,2-dichloroethane; tertiary amides, such as N,N-dimethylformamide, N,N-dimethylacetamide and N-methylpyrrolidone; acetonitrile; and mixtures of these solvents. The reaction is often carried out at the reflux temperature of the solvent, or in a pressure vessel.

The time course of the reaction varies according to a number of factors, such as the reactivity and concentration of the reactants, and the reaction temperature. As will be appreciated by one skilled in the art, the reaction proceeds faster at higher temperatures and relatively short reaction times are used, whereas at lower temperatures the reaction proceeds more slowly and longer reaction times are required, in order to obtain a good yield of product. Having full regard for these factors, when working at about 100°C, reaction times of several hours, for example from about 2 hours to about 24 hours are typically used.

The reagents are usually contacted in substantially equimolar proportions, although use of an excess of either component will successfully lead to the formation of product. However, in the case wherein X is chloro or bromo, it is advisable to use at least two molar equivalents of the amine of formula $R^3$—N-H—$(CH_2)_nR^4$, in order consume the HX liberated. Alternatively, at least one equivalent of an inorganic base, e.g. sodium carbonate, or a tertiary amine, such as triethylamine or pyridine, can be added to function as the acid-binder.

The product can be isolated and purified in conventional manner, e.g. by filtration if necessary to remove solids, evaporation to small volume under reduced pressure, basification (e.g. with sodium hydroxide or sodium bicarbonate), extraction into a suitable solvent (e.g. chloroform), separation of the orgaic phase, washing with water, drying, evaporation under reduced pressure to yield the crude product and recrystallization from a suitable solvent, e.g. ethanol. If desired, an acid-addition salt may be prepared from the crude or pure free base product by the conventional technique of reacting the free base with the acid in an inert solvent, e.g. by mixing alcoholic solutions of each and collecting the resulting precipitate by filtration. The product may then be recrystallized to purity.

Method B, which is in fact a variation of Method A, is useful specifically for preparation of those compounds of formula I, wherein $R^6$ is hydroxy. In this case, the procedure of Method A is used, but utilizing as starting material a compound of formula II, wherein the hydroxy group at C-6 is replaced by a protected hydroxy group, followed, at the end of the reaction, by removal of the protecting group. The protecting group is removed by conventional procedures, e.g. mild hydrolysis or hydrogenation. A particularly suitable protecting group is a lower alkoxycarbonyl group e.g. the ethoxycarbonyl group, which is conveniently removed in the final reaction stage by treating the appropriate protected compound with an aqueous ammonia solution together with sufficient organic solvent, e.g. ethanol, for complete dissolution. Heating is not usually required, and the deprotected product can be isolated by evaporation of the solution in vacuo to dryness and crystallization of the residual solid from a suitable solvent, e.g. methanol. The free base or salt form of the product can be obtained as required using the conventional technique. An alternative suitable protecting group is the benzyl group, which can be removed in the final stage by a conventional hydrogenation technique.

Method C, which is also a variation of Method A, is useful specifically for the preparation of those compounds of formula I, wherein $R^6$ is amino. In Method C, the procedure of Method A is again used, but utilizing as starting material the appropriate quinazoline compound with a nitro group at the C-6 position, followed at the end of the reaction, by reduction of the said nitro group to an amino group. The reduction is suitably effected with the free base or salt dissolved in a suitable solvent, e.g. glacial acetic acid, and the hydrogenation being carried out at ambient temperature and at low pressure, e.g. 50 p.s.i. in the presence of Raney nickel as catalyst. The product may then be recovered by filtration of the reduction solution to remove the catalyst, evaporation of the filtrate to dryness and purification and optional free base or salt formation by conventional technique.

Method D is useful for the preparation of the compounds of formula I, wherein $R^6$ is alkoxy, and it comprises the alkylation the corresponding compound of formula I, wherein $R^6$ is hydroxy. The alkylation is carried out, for example, by conversion of the phenolic hydroxy group to its sodium or potassium salt, e.g. using sodium hydride, sodium methoxide or potassium methoxide, followed by reaction of the salt with an alkyl halide, for example, and alkyl iodide. Other techniques known in the art for the alkylation of phenols can also be used (consult Buehler and Pearson, "Survey of Organic Synthesis," Wiley-Interscience, 1970, pp. 285–289).

Method E is useful specifically for the compounds of formula I, wherein $R^3$ is hydrogen. The method comprises the catalytic hydrogenolysis of the corresponding compound of formula I, wherein $R^3$ is benzyl. Techniques for catalytic hydrogenolysis are well-known in the art. Consult House, "Modern Synthetic Reactions," W. A. Benjamin, Inc., New York-Amsterdam, 1965, pp. 10–12, and references cited.

Method F, which is a further variation of Method A, is useful specifically for the preparation of the compounds for formula I, wherein $R^2$ is hydroxyalkyl. In this case, the procedure of Method A is used, but employing as the quinazoline starting material, the corresponding compound wherein the hydroxy group in the substituent at C-2 is protected by an alkanoyl group, e.g. an acetyl group, followed by removal of the protecting group by a conventional procedure, e.g. by mild hydrolysis. The hydrolytic step and obtention of the product are suitably effected in a similar way as described in Method B, or employing a solvent extraction technique in place of evaporation of the reaction solution in vacuo to dryness described therein.

The compounds of formula II used as starting materials in each of the above methods are either known compounds, or they are obtainable by well-documented routes by analogous procedures. For example, the compounds of formula II are obtainable from the corresponding 3,4-dihydro-4-oxoquinazolines of formulia IV, which in turn are prepared from the requisite anthranilic acids (III). Refer to British Pat. No. 1,199,768; U.S. Pat. Nos. 3,511,836 and 3,669,968; Armarego in "Fused Pyrimidines, Part I, Quinazolines," Volume 24 of "The Chemistry of Heterocyclic Compounds," Arnold Weissberger, editor, Interscience Publishers, New York-London-Sydney, 1967.

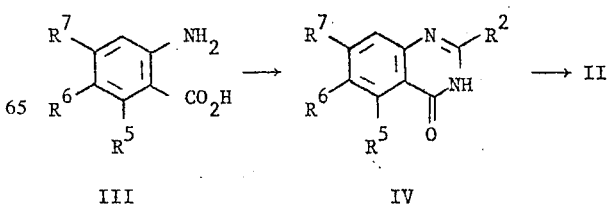

The compounds of the invention containing one or more asymmetric centers will exist as one or more pairs of enantiomers, and such pairs of individual isomers may be separable by physical methods, e.g. by fractional crystallization or chromatography of the free bases or suitable salts. The invention includes the separated pairs as well as mixtures thereof, as recemic mixtures or as separated D- and L-opticaly-active isomeric forms.

A characteristic feature of the quinazoline compounds of this inventon is their ability to form acid-addition salts, and all such salts are to be considered within the scope and purview of this invention. Although when contemplating therapeutic use of a compound of this invention, it is advisable to use a pharmaceutically-acceptable salt, other salts can be used for a variety of other purposes, such as for example, isolating amd purifying individual compounds of the invention, and interconverting pharmaceutically-acceptable salts with their non-salt counterparts. Pharmaceuticaly-acceptable acid-addition salts of the compounds of the invention are those formed from acids which form non-toxic acid-addition salts, containing pharmaceutically-acceptable anions, such as the hydrochloride, hydrobromide, hydroiodide, sulfate or bisulfate, phosphate or acid phosphate, acetate, maleate, fumarate, oxalate, lactate, tartrate, citrate, gluconate, saccharate and p-toluenesulfonate salts. As will be appreciated by one skilled in the art, several of the quinazoline compounds form salts which incorporate more than one equivalent of the acid component, and these salts are also within the scope of the invention.

The cardiac stimulant activity of the compounds of the invention is shown by their effectiveness in one or more of the following tests: (a) increasing the force of contraction in the isolated, spontaneously beating, guinea pig double atria preparation; (b) increasing the maximum rate of development of left ventricular pressure, dp/dt (max.), in the anaesthetized dog with an implanted left ventricular catheter; (c) increasing dp/dt (max.) in the conscious dog with an implanted left ventricular transducer.

In test (a) the inotropic and chronotropic response of the atria to the test compound are measured at several doses and compared with the responses elicited by isoprenaline. The comparison of the dose response curves obtained gives a measure of the selectivity of the test compound for increasing the force rather than the rate of myocardia contraction.

In test (b) the action of the test compound following intravenous administration is measured in the anaesthetized dog and compared with that of isoprenaline. The potency of the inotropic action, the selectivity for increase in force rather than rate of contraction, and the duration of action of the inotropic effect of the test compound are obtained, as are also its peripheral effects, e.g. the effect on the blood pressure.

In test (c) the action of the test compound following either intravenous or oral administration to the conscious dog with an implanted left ventricular transducer is measured and compared with that of isoprenaline. As in test (b) the potency of the inotropic action, the selection for increase in force rather than rate of contraction, and the duration of action of the inotropic effect of the test compound are all obtained.

The quinazoline compounds of this invention are cardiac stimulants, and they are usefull in the curative or prophylactic treatment of cardiac conditions such as congestive heart failure, augina pectoris, cardiac arrhythmias and acute heart failure. Several particularly desirable members selectively increase the force of myocardial contraction withut producing significant increase in heart rate.

By virtue of their performance in tests (a) to (c), the preferred compounds of this invention are those of formula I, wherein $R^4$ is pyridyl, particularly 2-pyridyl. More specifically, preferred compounds are those of formula I, wherein $R^4$ is pyridyl, $R^2$ is hydrogen or methyl, $R^5$ is hydrogen, $R^6$ and $R^7$ are each alkoxy having from one to six carbon atoms, and n is 2.

The compounds of the invention can be administered alone, but they will generally be administered in admixture with a pharmaceutical carrier selected with regard to the intended route of administration and standard pharmaceutical practice. For example, they can be administered orally in the form of tablets containing such excipients as starch or lactose, or in capsule either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, oral dosages will be in the range from 100 mg. to 1g. daily, taken in 3 or 4 divided doses per day, for an average adult patient (70 kg.). Dosages for intravenous administration will be within the range 5 to 300 mg. per single dose as required, for example in the treatment of acute heart failure. Thus, for a typical adult patient, individual tablets or capsules will contain from 25 to 350 mg. of active compound, in a suitable pharmaceutically-acceptable vehicle or carrier. The physician in any event will determine the actual dosage which will be most suitable for an individual patient, and it will vary with the age, weight and response of that patient.

It has been found, as a result of more intensive testing, that one of the compounds of this invention, namely 6,7-dimethoxy-4-(N-methyl-2 [2-pyridyl]ethylamino)quinazoline, exhibits nephrotoxicity when administered either orally or parenterally to dogs. However, nephrotoxic effects are not observed when this compound is administered to mice, rats or rabbits.

The invention is illustrated by the following examples, in which all temperatures are given in °C.

EXAMPLE I 6,7-Dimethoxy-4-(N-methyl-2-[2-pyridyl]ethylamino)quinazoline

A mixture of 4-chloro-6,7-dimethoxyquinazoline (30.3g.), 2-(2-[N-methylamino]ethyl)pyridine (18.4g.), triethylamine (38.8g.) and ethanol (200ml.) was refluxed for 8 hours, after which the hot mixture was filtered and the filtrate evaporated in vacuo to dryness. Trituration of the residue in aqueous sodium carbonate solution (10%, 300ml.) produced a solid which was extracted in chloroform, and evaporation of the chloroform solution in vacuo afforded a yellow solid. The latter was washed with petroleum ether (40°–60°), dried and crystallized from aqueous ethanol solution to give the free base form of the product, m.p. 90°–97° (40g.).

To a solution of the free base in the minimum quantity of hot ethanol was added concentrated hydrochloric acid. On standing 6,7-dimethoxy-4-(N-methyl-2-[2-pyridyl]ethylamino)quinazoline dihydrochloride monohydrate, m.p. 233°–237° crystallized out.

Analysis — Calcd. for $C_{18}H_{20}N_4O_2 \cdot 2HCl \cdot H_2O$ (percent): C, 52.05; H, 5.82; N, 13.49. Found (percent): C, 51.86; H, 5.70; N, 13.6.

EXAMPLE II

The following compounds were prepared, using the general method of Example I, from the appropriate 4-chloroquinazoline derivative and heterocycle-substituted alkylamine, and isolated either as the free base or as a salt, formed by addition of the appropriate acid to a solution of the base, the product in some cases being hydrated, as indicated.

TABLE I

$R^3-N-(CH_2)n-R^4$

| $R^2$ | $R^3$ | n | $R^4$ | Salt/Free Base/Hydrate m.p. °C | Analysis % (Theoretical in brackets) C | H | N |
|---|---|---|---|---|---|---|---|
| H | H | 2 | 2-pyridyl | free base, 170–3° | 65.53 | 5.15 | 17.87 |
|  |  |  |  |  | (65.79 | 5.85 | 18.05) |
| H | H | 2 | 4-pyridyl | free base, 200–202° | 65.64 | 5.90 | 18.08 |
|  |  |  |  |  | (65.79 | 5.85 | 18.05) |
| $CH_3$ | H | 2 | 2-pyridyl | free base, 159–161° | 66.83 | 6.26 | 17.18 |
|  |  |  |  |  | (66.65 | 6.22 | 17.27) |
| H | $C_6H_5CH_2$ | 2 | 2-pyridyl | free base, 145–7° | 72.38 | 6.08 | 14.08 |
|  |  |  |  |  | (71.98 | 6.04 | 13.99) |
| $CH_3CH_2$ | H | 2 | 2-pyridyl | free base, 124–6° | 67.15 | 6.16 | 16.37 |
|  |  |  |  |  | (67.43 | 6.55 | 16.56) |
| $(CH_3)_2CH$ | H | 2 | 2-pyridyl | ¼-hydrate, 152–3° | 67.56 | 6.82 | 15.69 |
|  |  |  |  |  | (67.30 | 6.92 | 15.70) |
| $CH_3CH_2$ | $CH_3$ | 2 | 2-pyridyl | dimaleate, 148–9° | 57.33 | 5.56 | 9.68 |
|  |  |  |  |  | (57.53 | 5.52 | 9.59) |
| H | H | 3 | 2-pyridyl | free base, 180–183° | 66.39 | 6.11 | 17.64 |
|  |  |  |  |  | (66.65 | 6.22 | 17.27) |
| $CH_3$ | $CH_3$ | 2 | 2-pyridyl | dihydrochloride hemihydrate, 279–280° | 53.12 | 6.26 | 13.73 |
|  |  |  |  |  | (54.29 | 6.00 | 13.33) |
| $CH_3$ | $CH_3CH_2$ | 2 | 2-pyridyl | hydrochloride sesquihydrate, 261–2° | 57.46 | 6.58 | 13.39 |
|  |  |  |  |  | (57.75 | 6.79 | 13.47) |
| $CH_3$ | $n$-$C_4H_9$ | 2 | 2-pyridyl | dihydrochloride ¼-hydrate, 246–8° | 58.12 | 6.70 | 12.51 |
|  |  |  |  |  | (57.70 | 6.71 | 12.24) |
| $(CH_3)_2CH$ | $CH_3$ | 2 | 2-pyridyl | dimaleate, 135–8° | 57.89 | 5.72 | 9.57 |
|  |  |  |  |  | (58.19 | 5.73 | 9.36) |
| $CH_3$ | $CH_3$ | 2 | 4-pyridyl | ¼-hydrate, 100–105° | 66.78 | 6.33 | 16.27 |
|  |  |  |  |  | (66.55 | 6.61 | 16.34) |
| $CH_3$ | $CH_3$ | 3 | 2-pyridyl | dihydrochloride, 222–5° | 56.29 | 6.24 | 12.97 |
|  |  |  |  |  | (57.46 | 6.16 | 13.17) |
| $CH_3OCH_2$ | $CH_3$ | 2 | 2-pyridyl | dimaleate, 130–132° | 56.18 | 5.49 | 9.57 |
|  |  |  |  |  | (55.99 | 5.37 | 9.32) |
| H | $n$-$C_3H_7$ | 2 | 2-pyridyl | free base, 102–3° | 68.30 | 7.01 | 15.76 |
|  |  |  |  |  | (68.16 | 6.86 | 15.90) |
| H | p-$CH_3O$- | 2 | 2-pyridyl | Free base, 149–151° | 69.21 | 5.81 | 13.45 |
|  |  |  |  |  | (69.13 | 5.86 | 13.70) |
| H | $CH_3$ | 4 | 3-pyridyl | oxalate sesquihydrate 159–161° | 57.05 | 5.67 | 11.47 |
|  |  |  |  |  | (56.66 | 5.58 | 11.49) |
| H | $CH_3$ | 1 | 3-pyridyl | dihydrochloride, 210–212° | 53.07 | 5.44 | 14.30 |
|  |  |  |  |  | (53.27 | 5.27 | 14.61) |
| H | $CH_3$ | 1 | 4-pyridyl | free base, 152–4° | 65.75 | 5.78 | 17.06 |
|  |  |  |  |  | (65.79 | 5.85 | 18.05 |
| H | $CH_3$ | 2 | 2-pyridyl | hemihydrate, 86–8° | 65.05 | 6.32 | 16.79 |
|  |  |  |  |  | (64.84 | 6.35 | 16.81) |
| H | $CH_3$ | 2 | 5-ethyl-2-pyridyl | dihydrochloride, 222–4° | 55.51 | 6.11 | 13.48 |
|  |  |  |  |  | (56.46 | 6.16 | 13.17) |
| H | $CH_3$ | 2 | 4-methyl-2-pyridyl | free base, 123–6° | 67.06 | 6.58 | 16.44 |
|  |  |  |  |  | (67.43 | 6.55 | 16.56) |
| H | $CH_3$ | 2 | 6-methyl-2-pyridyl | free base, 88–90° | 67.13 | 6.53 | 16.82 |
|  |  |  |  |  | (67.44 | 6.55 | 16.56) |
| H | $CH_3$ | 2 | 2-methyl-4-thiazolyl | dihydrochloride 205–8° | (48.52 | 5.61 | 13.30 |
|  |  |  |  |  | (48.93 | 5.31 | 13.43) |
| H | H | 2 | 4-imidazolyl | free base, 225–233° | 60.49 | 5.88 | 23.36 |
|  |  |  |  |  | (60.19 | 5.72 | 23.40) |
| H | $CH_3$ | 2 | 4-methyl-5-thiazolyl | free base, 127–9° | 59.20 | 5.74 | 16.03 |
|  |  |  |  |  | (59.29 | 5.85 | 16.27) |
| H | $CH_3$ | 2 | 2-quinolyl | dihydrochloride, 242–6° | 58.45 | 5.59 | 12.41 |
|  |  |  |  |  | (59.07 | 5.41 | 12.52) |
| H | $C_2H_5$ | 2 | 2-pyrazinyl | free base, 134–7° | 63.24 | 6.20 | 20.96 |
|  |  |  |  |  | (63.70 | 6.24 | 20.63) |
| H | H | 1 | 2-hydroxy-4-methyl-3-pyridyl | free base, 297–8° | 62.32 | 5.42 | 17.12 |
|  |  |  |  |  | (62.56 | 5.56 | 17.17) |
| H | H | 2 | 3-indolyl | free base 196° | 67.80 | 6.05 | 17.92 |

TABLE I-continued

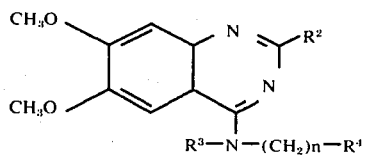

| R² | R³ | n | R⁴ | Salt/Free Base/Hydrate m.p. °C | Analysis % (Theoretical in brackets) C | H | N |
|---|---|---|---|---|---|---|---|
| | | | | | (67.85 | 5.95 | 17.98 |

TABLE II

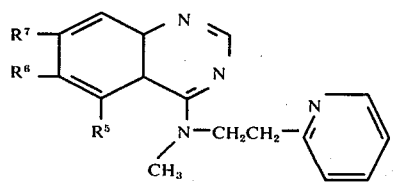

| R⁵ | R⁶ | R⁷ | Salt/Free Base/Hydrate m.p. °C | Analysis% (theoretical in brackets) C | H | N |
|---|---|---|---|---|---|---|
| H | H | CH₃O | dihydrochloride sesquihydrate, 215–7° | (52.52 | 5.95 | 14.22 |
|   |   |   |   | 52.38 | 5.82 | 14.37) |
| CH₃ | CH₃O | CH₃O | dihydrochloride trihydrate, 189–192° | 49.23 | 5.55 | 12.17 |
|   |   |   |   | (49.04 | 5.50 | 12.04) |
| CH₃O | CH₃O | CH₃O | dihydrochloride 2 ¾-hydrate 164–7° | 47.78 | 5.23 | 11.82 |
|   |   |   |   | (47.86 | 6.23 | 11.75) |

EXAMPLE III 6,7-Dimethoxy-4-(N-methyl-2-[2-pyridyl]prop-1-ylamino)quinazoline Reaction of 6,7-dimethoxy-4-chloroquinazoline with 2-(1-[N-methylamino]prop-2-yl)pyridine, according to the procedure of Example I, afforded the title compound, isolated as its dihydrochloride trihydrate, m.p. 235°C.

Analysis: Calcd. for C₁₉H₂₂N₄O₂.2HCl.3H₂O (percent): C, 49.04; H, 6.50; N, 12.04. Found (percent): C, 49.35; H, 5.72; N, 12.01.

EXAMPLE IV 6,7-Dimethoxy-4-(N-methyl-1-[2-pyridyl]prop-2-ylamino)quinazoline Reaction of 6,7-dimethoxy-4-chloroquinazoline with 2-(2-[N-methylamino]prop-1-yl)pyridine, according to the procedure of Example I, yielded the title compound, isolated as its dihydrochloride dihydrate, m.p. 242°–5°C.

Analysis: Calcd. for C₁₉H₂₂N₄O₂.2HCl.2H₂O (percent): C, 51.01; H, 6.31; N, 12.53. Found (percent): C, 50.88, H, 6.06; N, 12.59.

EXAMPLE V

Reaction of the appropriate 4-chloroquinazoline with the requisite heterocycle-substituted amine, substantially according to the procedure of Example I, provides the following congeners:

TABLE III

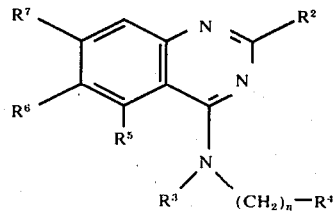

| R₂ | R³ | R⁴ | R⁵ | R⁶ | R⁷ | n |
|---|---|---|---|---|---|---|
| H | CH₃CH₂ | 2-pyridyl | H | CH₃O | CH₃O | 2 |
| H | CH₃(CH₂)₂CH₂ | 4-pyridyl | H | CH₃O | CH₃O | 2 |
| H | CH₃(CH₂)₃CH₂ | 3-pyridyl | H | CH₃O | CH₃O | 2 |

TABLE III-continued

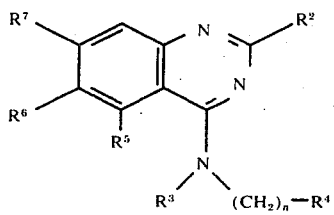

| R₂ | R³ | R⁴ | R⁵ | R⁶ | R⁷ | n |
|---|---|---|---|---|---|---|
| $CH_3$ | $CH_3(CH_2)_4CH_2$ | 2-thiazolyl | H | $CH_3O$ | $CH_3O$ | 1 |
| $CH_3$ | $C_6H_5CH_2$ | 2-quinolyl | H | $CH_3O$ | $CH_3O$ | 2 |
| $CH_3CH_2$ | $C_6H_5$ | 4-ethyl-2-pyridyl | H | $CH_3O$ | $CH_3O$ | 1 |
| $CH_3CH_2CH_2$ | $m\text{-}CH_3OC_6H_4$ | 2-thiazolyl | H | $CH_3O$ | $CH_3O$ | 3 |
| $CH_3(CH_2)_2CH_2$ | $p\text{-}CH_3CH_2OC_6H_4$ | 2-pyridyl | H | $CH_3O$ | $CH_3O$ | 4 |
| $CH_3(CH_2)_3CH_2$ | H | 3-pyridyl | H | $CH_3CH_2O$ | $CH_3CH_2O$ | 1 |
| $CH_3(CH_2)_4CH_2$ | $CH_3$ | 2-indolyl | H | $CH_3CH_2O$ | $CH_3CH_2O$ | 3 |
| $CH_3OCH_2$ | $CH_3CH_2$ | 2-imidazolyl | H | $CH_3CH_2O$ | $CH_3CH_2O$ | 2 |
| $CH_3CH_2OCH_2$ | $C_6H_5CH_2$ | 2-pyridyl | H | $CH_3CH_2O$ | $CH_3CH_2O$ | 2 |
| $CH_3CH_2CH_2OCH_2$ | $C_6H_5$ | 4-n-propyl-2-pyridyl | H | $CH_3CH_2O$ | $CH_3CH_2O$ | 2 |
| $CH_3(CH_2)_4OCH_2$ | $o\text{-}CH_3OC_6H_4$ | 4-ethyl-5-thiazolyl | H | $CH_3(CH_2)_2O$ | $CH_3(CH_2)_2O$ | 1 |
| H | $C_6H_5CH_2$ | 4-pyridyl | H | $(CH_3)_2CHO$ | $(CH_3)_2CHO$ | 1 |
| H | $C_6H_5$ | 5-n-hexyl-2-pyridyl | H | $CH_3(CH_2)_3O$ | $CH_3(CH_2)_3O$ | 2 |
| H | $p\text{-}CH_3(CH_2)_3OC_6H_5$ | 3-pyridyl | H | $CH_3(CH_2)_3O$ | $CH_3(CH_2)_3O$ | 3 |
| $CH_3$ | H | 2-pyridyl | H | $CH_3(CH_2)_3O$ | $CH_3(CH_2)_3O$ | 2 |
| $CH_3$ | $CH_3$ | 2-indolyl | H | $CH_3(CH_2)_3O$ | $CH_3(CH_2)_3O$ | 2 |
| $CH_3CH_2$ | $C_6H_5CH_2$ | 2-hydroxy-3-pyridyl | H | $CH_3(CH_2)_3O$ | $CH_3(CH_2)_3O$ | 2 |
| $CH_3CH_2CH_2$ | $C_6H_5$ | 2-pyridyl | H | $CH_3(CH_2)_4O$ | $CH_3(CH_2)_4O$ | 1 |
| $CH_3(CH_2)_2CH_2$ | $m\text{-}CH_3CH_2OC_6H_5$ | 3-pyridyl | H | $CH_3(CH_2)_4O$ | $CH_3(CH_2)_4O$ | 3 |
| $CH_3(CH_2)_3CH_2$ | H | 4-n-butyl-5-thiazolyl | H | $CH_3(CH_2)_4O$ | $CH_3(CH_2)_4O$ | 2 |
| $CH_3(CH_2)_4CH_2$ | H | 4-quinolyl | H | $CH_3(CH_2)_4O$ | $CH_3(CH_2)_4O$ | 4 |
| $CH_3OCH_2$ | H | 2-pyridyl | H | $CH_3(CH_2)_5O$ | $CH_3(CH_2)_5O$ | 3 |
| $CH_3CH_2OCH_2$ | H | 2-pyrazinyl | H | $CH_3(CH_2)_5O$ | $CH_3(CH_2)_5O$ | 2 |
| $CH_3(CH_2)_2OCH_2$ | $CH_3$ | 3-indolyl | H | $CH_3(CH_2)_5O$ | $CH_3(CH_2)_5O$ | 2 |
| $CH_3(CH_2)_4OCH_2$ | $CH_3$ | 4-n-hexyl-5-thiazolyl | H | $(CH_3)_3CCH_2CH_2O$ | $(CH_3)_3CCH_2CH_2O$ | 3 |
| H | $CH_3$ | 2-pyridyl | H | $CH_3O$ | $CH_3CH_2O$ | 2 |
| H | $CH_3$ | 2-pyridyl | H | $CH_3CH_2O$ | $CH_3O$ | 2 |
| H | $C_6H_5CH_2$ | 3-pyridyl | $CH_3O$ | H | $CH_3O$ | 1 |
| $CH_3$ | $C_6H_5$ | 4-pyridyl | $CH_3O$ | H | $CH_3O$ | 2 |
| $CH_3$ | $m\text{-}CH_3OC_6H_5$ | 2-thiazolyl | $CH_3O$ | H | $CH_3O$ | 2 |
| $CH_3CH_2$ | H | 4-methyl-2-pyridyl | $CH_3CH_2O$ | H | $CH_3CH_2O$ | 2 |
| $CH_3CH_2CH_2$ | H | 2-pyridyl | $CH_3CH_2O$ | H | $CH_3CH_2O$ | 3 |
| $(CH_3)_2CH$ | $CH_3$ | 2-quinolyl | $CH_3(CH_2)_2O$ | H | $CH_3(CH_2)_2O$ | 1 |
| $CH_3(CH_2)_2CH_2$ | $CH_3$ | 2-pyrazinyl | $CH_3(CH_2)_3O$ | H | $CH_3(CH_2)_3O$ | 2 |
| $CH_3(CH_2)_3CH_2$ | $CH_3CH_2$ | 2-hydroxy-3-pyridyl | $CH_3(CH_2)_5O$ | H | $CH_3(CH_2)_5O$ | 3 |
| $CH_3OCH_2$ | H | 2-pyridyl | $CH_3$ | H | $CH_3O$ | 2 |
| $CH_3OCH_2CH_2$ | $CH_3$ | 3-pyridyl | $CH_3CH_2$ | H | $CH_3O$ | 1 |
| $CH_3(CH_2)_2OCH_2$ | $CH_3(CH_2)_3CH_2$ | 2-methyl-4-thiazolyl | H | $CH_3CH_2CH_2$ | $CH_3O$ | 2 |
| $CH_3(CH_2)_4OCH_2$ | $C_6H_5CH_2$ | 2-quinolyl | H | $(CH_3)_2CH$ | $CH_3CH_2O$ | 3 |
| H | $p\text{-}CH_3(CH_2)_5OC_6H_5$ | 2-pyridyl | $CH_3$ | H | $CH_3O$ | |
| H | H | 3-pyridyl | $CH_3CH_2$ | H | $CH_3O$ | |
| H | H | 4-pyridyl | $CH_3CH_2CH_2$ | H | $CH_3CH_2O$ | |
| $CH_3$ | $CH_3$ | 2-quinolyl | $CH_3(CH_2)_4CH_2$ | H | $CH_3O$ | |
| $CH_3$ | $CH_3CH_2$ | 2-pyridyl | $CH_3$ | $CH_3$ | $CH_3O$ | |
| $CH_3$ | $o\text{-}CH_3OC_6H_5$ | 2-pyridyl | $CH_3O$ | $CH_3O$ | $CH_3O$ | |
| $CH_3$ | H | 2-quinolyl | $CH_3CH_2O$ | $CH_3CH_2O$ | $CH_3CH_2O$ | |
| $CH_3$ | $CH_3$ | 2-imidazolyl | $CH_3CH_2CH_2O$ | $CH_3CH_2CH_2O$ | $CH_3CH_2CH_2O$ | |
| $CH_3$ | $CH_3$ | 6-methyl-2-pyridyl | $CH_3(CH_2)_5O$ | $CH_3(CH_2)_5O$ | $CH_3(CH_2)_5O$ | |

EXAMPLE VI

6-Hydroxy-7-methoxy-4-(N-methyl-2-[2-pyridyl]ethylamino)quinazoline

A mixture of 4-chloro-6-ethoxycarbonyloxy-7-methoxyquinazoline (3 g), 2-(2-[N-methylamino]ethyl)pyridine (1.44 g), triethylamine (2 ml) and ethanol (15 ml) was refluxed for 3 hours, after which the mixture was filtered and the filtrate evaporated in vacuo to dryness. The residue was treated with aqueous sodium bicarbonate solution, the whole then being extracted with chloroform and the chloroform solution separated and dried over anhydrous magnesium sulphate. Evaporation of the dried chloroform solution in vacuo afforded a syrup, and this was triturated in ethanol giving some solid which was collected by filtration. The filtrate was evaporated in vacuo and the residue was triturated in chloroform, the resulting solid then being collected by filtration and the filtrate evaporated in vacuo to a syrup.

Thin-layer chromatographic evidence indicated that of the two solids and a syrup produced by the above procedure, the syrup consisted of a crude form of the desired product, 6-ethoxycarbonyloxy-7-methoxy-4-(N-methyl-2-[2-pyridyl]ethylamino)quinazoline, which was suitable for immediate use in the next and final stage.

The crude product of the previous stage and concentrated aqueous ammonium hydroxide solution (10 ml) were added to ethanol (20 ml) and the mixture was allowed to stand at room temperature over 3 days. The reaction solution was then evaporated in vacuo to dryness, the resulting semi-solid dissolved in methanol and ethereal hydrogen chloride added, and this evaporated to dryness and the residue triturated in isopropanol, affording a brown solid. Recrystallization of the latter first from aqueous isopropanol and then from methanol yielded 6-hydroxy-7-methoxy-4-(N-methyl-2-[2-pyridyl]ethyl-amino)quinazoline dihydrochloride 1 ¼ hydrate, m.p. 226-9°C (dec).

Analysis: Calcd. for $C_{17}H_{18}N_4O_2.2HCl$ 1 ¼ $H_2O$ (percent): C, 40.31; H, 5.59; N, 13.81. Found (percent): C, 40.01; H, 5.28; N, 14.04.

EXAMPLE VII

Reaction of the appropriate 4-chloro-6-ethoxycarbonyloxy-7-alkoxyquinazoline with the requisite heterocycle-substituted amine, followed by treatment of the product with ammonia, substantially according to the procedure of Example VI, affords the following compounds.

TABLE IV

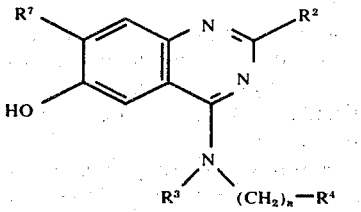

| $R^2$ | $R^3$ | $R^4$ | $R^7$ | n |
|---|---|---|---|---|
| H | m-$CH_3CH_2OC_6H_4$ | 2-pyridyl | $CH_3O$ | 2 |
| $CH_3$ | H | 3-pyridyl | $CH_3O$ | 2 |
| $CH_3CH_2$ | $CH_3$ | 4-pyridyl | $CH_3O$ | 1 |
| $CH_3CH_2CH_2$ | $C_6H_5CH_2$ | 2-thiazolyl | $CH_3O$ | 2 |
| $CH_3(CH_2)_3$ | $C_6H_5$ | 2-indolyl | $CH_3O$ | 2 |
| $CH_3(CH_2)_4$ | H | 2-pyridyl | $CH_3CH_2O$ | 3 |
| $CH_3(CH_2)_5$ | $CH_3$ | 4-pyridyl | $CH_3CH_2O$ | 2 |
| H | $CH_3CH_2$ | 2-pyrazinyl | $CH_3(CH_2)_2O$ | 2 |
| H | $C_6H_5CH_2$ | 2-pyridyl | $CH_3(CH_2)_2O$ | 1 |
| $CH_3$ | $C_6H_5$ | 2-quinolyl | $(CH_3)_2CHO$ | 3 |
| $CH_3$ | p-$CH_3OC_6H_4$ | 2-pyridyl | $CH_3(CH_2)_3O$ | 2 |
| $CH_3CH_2$ | $CH_3$ | 2-imidazolyl | $CH_3(CH_2)_3O$ | 4 |

EXAMPLE VIII

6-Amino-7-methoxy-4-(N-methyl-2-[2-pyridyl]ethylamino)quinazoline

A mixture of 4-chloro-7-methoxy-6-nitroquinazoline (19.0 g), 2-(2-[N-methylamino]ethyl)pyridine (11.25 g), triethylamine (17 g) and ethanol (300 ml) was refluxed for 1 1/2 hours and the reaction mixture evaporated in vacuo to dryness. The residue was triturated in aqueous sodium bicarbonate solution and the yellow solid formed was subsequently extracted into chloroform. Evaporation of the dried organic solution afforded a solid which was recrystallized three times from ethyl acetate giving 10.1 g of 7-methoxy-6-nitro-4-(N-methyl-2-[2-pyridyl]ethylamino)quinazoline.

To a solution of the nitro compound (18 g, comprising the product of the previous stage and a further quantity produced similarly) in glacial acetic acid was added Raney nickel catalyst, and the mixture was submitted to hydrogenation at room temperature at 50 p.s.i. pressure until the theoretical amount of hydrogen had been used in the reaction. The mixture was filtered to remove catalyst and the filtrate evaporated in vacuo to dryness. The residue was dissolved in water, the aqueous solution basified by addition of iced aqueous ammonium hydroxide solution, and the solution extracted with chloroform. Evaporation of the previously dried (anhydrous potassium carbonate) organic solution in vacuo afforded a grey solid (15 g), a sample of which was converted to the hydrochloride salt by the conventional technique and recrystallized from isopropanol containing a little water. This produced 6-amino-7-methoxy-4-(N-methyl-2-[2-pyridyl]ethylamino)-quinazoline dihydrochloride monohydrate, m.p. 290°C (dec).

Analysis: Calcd. for $C_{17}H_{19}N_5O.2HCl.H_2O$ (percent): C, 51.00; H, 5.79; N, 17.50. Found (percent): C, 51.43; H, 5.72; N, 17.72.

EXAMPLE IX

Reaction of 4-chloro-7-methoxy-6-nitroquinazoline with the appropriate heterocycle-substituted amine, followed by reduction of the product so produced with hydrogen in the presence of Raney nickel, substantially according to the procedure of Example VIII, affords the following compounds:

TABLE V

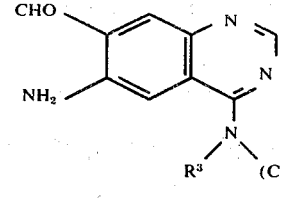

| $R^3$ | $R^4$ | n |
|---|---|---|
| H | 2-pyridyl | 2 |
| H | 3-pyridyl | 2 |
| H | 4-pyridyl | 2 |
| $CH_3$ | 2-pyridyl | 3 |
| $CH_3$ | 2-indolyl | 2 |
| $CH_3CH_2$ | 2-quinolyl | 2 |
| $CH_3CH_2$ | 2-pyridyl | 4 |
| $CH_3(CH_2)_2$ | 2-imidazolyl | 2 |
| $CH_3(CH_2)_3$ | 2-pyridyl | 2 |
| $CH_3(CH_2)_5$ | 2-pyridyl | 1 |

EXAMPLE X

6,7-Dimethoxy-2-hydroxymethyl-4-(N-methyl-2-[2-pyridyl] ethylamino) quinazoline A mixture of 2-acetoxymethyl-4-chloro-6,7-dimethoxyquinazoline (4.1 g), 2-(2-[N-methylamino]ethyl)pyridine (2.3 g), triethylamine (100 ml) and dimethylacetamide (100 ml) was stirred at room temperature for 22 hours and then evaporated in vacuo to dryness. The residue was extracted with chloroform and the organic solution washed with saturated aqueous sodium bicarbonate solution and dried over anhydrous sodium sulphate. Removal of the solvent by evaporation afforded a brown oil, and this was triturated in diethyl ether to give a brown solid and a mother liquor which on treatmemt with a solution of maleic acid in ethyl acetate yielded a yellow solid. The latter was collected by filtration and crystallized from isopropanol to give 4.0 g of 2-acetoxymethyl-6,7-dimethoxy-4-(N-methyl-2-[2-pyridyl]ethylamino)quinazoline dimaleate as a greenish-yellow solid, m.p. 128°-130° with decomposition.

To a stirred solution of the above product (2.4 g) in water (40 ml) was added aqueous sodium hydroxide solution (0.86 g solid in 25 ml water), which produced a fine white precipitate. After addition of sufficient methanol to dissolve the precipitate, the resulting yellow solution was stirred for 3 1/2 hours. The solution was then partially evaporated in vacuo to remove methanol, and the aqueous solution was extracted with chloroform. Evaporation in vacuo of the previously washed (water) and dried chloroform solution afforded a yellow oil. The latter was dissolved in ethyl acetate and to the solution was added ethereal hydrogen chloride solution until precipitation had been completed. After allowing the suspension to stand overnight in a refrigerator, the solid was collected by filtration and dried before being recrystallized twice from ethanol. This produced 6,7-dimethoxy-2-hydroxymethyl-4-(N-methyl-2-[2-pyridyl]ethylamino)quinazoline dihydrochloride, m.p. 264°–266°C.

Analysis: Calcd. for $C_{19}H_{22}N_4O_3 \cdot 2HCl$ (percent): C, 53.40; H, 5.66; N, 13.11. Found (percent): C, 53.07, H, 6.00; N, 13.99.

EXAMPLE XI

Reaction of the appropriate 2-acetoxyalkyl-4-chloro-6,7-dimethoxyquinazoline with the requisite heterocycle-substituted amine, following by hydrolysis, substantially according to the procedure of Example X, affords the following analogues:

TABLE VI

| $R^2$ | $R^3$ | $R^4$ | n |
|---|---|---|---|
| $HOCH_2$ | 2-pyridyl | H | 2 |
| $HOCH_2$ | 3-pyridyl | $CH_3$ | 2 |
| $HOCH_2$ | 4-pyridyl | $CH_3$ | 2 |
| $HOCH_2CH_2$ | 2-pyridyl | $C_6H_5CH_2$ | 2 |
| $HOCH_2CH_2$ | 2-pyridyl | $CH_3$ | 1 |
| $HOCH_2(CH_2)_2$ | 2-quinolyl | $CH_3$ | 3 |
| $HOCH_2(CH_2)_2$ | 2-indolyl | $pCH_3OC_6H_4$ | 2 |
| $HOCH_2(CH_2)_4$ | 2-thiazolyl | $CH_3$ | 2 |
| $HOCH_2(CH_2)_5$ | 2-pyridyl | $CH_3$ | 4 |

EXAMPLE XII

The following is an example of a typical parenteral formulation, intended for intravenous injection, in which the active ingredient is the compound of Example 1.

| | mg/ml |
|---|---|
| Active ingredient | 5.0 |
| Sodium chloride | 8.5 |
| Hydrochloric acid | Sufficient for pH adjustment |
| Water | Sufficient to bring correct volume |

The active ingredient and sodium chloride are dissolved in a little of the hydrochloric acid, and more of the latter is added until the pH of the solution is within the limits 3.75 ± 0.25, and the volume as nearly approaches the desired final volume as possible. Water is then added to bring the volume to the appropriate volume for the active ingredient and the salt to be present at the desired concentrations.

What is claimed is:

1. A compound of the formula

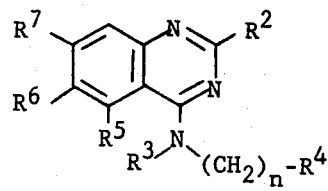

or a pharmaceutically acceptable acid-addition salt thereof;
wherein $R^2$ is selected from the group consisting of hydrogen, alkyl having from one to six carbon atoms, hydroxyalkyl having from one to six carbon atoms and alkoxyalkyl having from two to six carbon atoms;

$R^3$ is selected from the group consisting of hydrogen, benzyl, alkyl having from one to six carbon atoms, phenyl and alkoxyphenyl having from one to six carbon atoms in said alkoxy group;

$R^4$ is selected from the group consisting of pyridyl, quinolyl, thiazolyl, imidazolyl, pyrazinyl, indolyl, hydroxypyridyl, alkylpyridyl having from one to six carbon atoms in said alkyl group and alkylthiazolyl having from one to six carbon atoms in said alkyl group;

$R^5$ is hydrogen;

$R^6$ is selected from the group consisting of hydrogen, alkyl having from one to six carbon atoms, alkoxy having from one to six carbon atoms, hydroxy and amino;

$R^7$ is alkoxy having from one to six carbon atoms; and
$n$ is 1, 2, 3 or 4;
providing that $R^4$ is linked to $(CH_2)_n$ through a ring-carbon atom.

2. A compound according to claim 1, wherein $R^4$ is pyridyl.

3. A compound according to claim 2, wherein $R^6$ is said alkoxy.

4. A compound according to claim 3, wherein $R^6$ and $R^7$ are each methoxy.

5. A compound according to claim 4, wherein $R^2$ is selected from the group consisting of hydrogen and methyl.

6. A compound according to claim 5, wherein n is 2.

7. A compound according to claim 6, wherein $R^3$ is selected from the group consisting of hydrogen and methyl.

8. A compound according to claim 7, wherein $R^4$ is 2-pyridyl.

9. The compound according to claim 8, wherein $R^2$ is hydrogen and $R^3$ is methyl.

* * * * *

UNITED STATES PATENT AND TRADEMARK OFFICE
CERTIFICATE OF CORRECTION

PATENT NO. : 3,971,783
DATED : July 27, 1976
INVENTOR(S) : Ian Thompson Barnish et al It is certified that error appears in the above-identified patent and that said Letters Patent are hereby corrected as shown below:

Col. 7, the seventeenth entry in Table I under "$R^3$", "p-$CH_3O$" should read -- p-$CH_3O$ phenyl --.

Signed and Sealed this

Twenty-second Day of February 1977

[SEAL]

Attest:

RUTH C. MASON
*Attesting Officer*

C. MARSHALL DANN
*Commissioner of Patents and Trademarks*